(12) United States Patent
Weiland et al.

(10) Patent No.: US 9,084,584 B2
(45) Date of Patent: Jul. 21, 2015

(54) METHOD AND APPARATUS FOR SELECTING DIFFERENTIAL INPUT LEADS

(75) Inventors: James Martin Weiland, Greensburg, PA (US); Ronald Dean Fligge, Greensburg, PA (US); Louis Welty Hiener, III, Pittsburgh, PA (US); John Liston, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 22 days.

(21) Appl. No.: 14/122,270

(22) PCT Filed: Jun. 8, 2012

(86) PCT No.: PCT/IB2012/052902
§ 371 (c)(1),
(2), (4) Date: Nov. 26, 2013

(87) PCT Pub. No.: WO2012/168912
PCT Pub. Date: Dec. 13, 2012

(65) Prior Publication Data
US 2014/0194759 A1    Jul. 10, 2014

Related U.S. Application Data

(60) Provisional application No. 61/495,429, filed on Jun. 10, 2011.

(51) Int. Cl.
| | |
|---|---|
| A61B 5/04 | (2006.01) |
| A61B 5/00 | (2006.01) |
| A61B 5/0424 | (2006.01) |
| A61B 5/0428 | (2006.01) |
| A61B 5/0488 | (2006.01) |
| A61B 5/0496 | (2006.01) |
| A61B 5/0402 | (2006.01) |

(52) U.S. Cl.
CPC ............ *A61B 5/7221* (2013.01); *A61B 5/0402* (2013.01); *A61B 5/0424* (2013.01); *A61B5/0488* (2013.01); *A61B 5/0496* (2013.01); *A61B 5/04288* (2013.01); *A61B 5/4806* (2013.01)

(58) Field of Classification Search
CPC .. A61B 5/0488; A61B 5/0402; A61B 5/0424; A61B 5/04288; A61B 5/0496; A61B 5/4806; A61B 5/7221; A61B 5/053; A61B 5/0538
See application file for complete search history.

(56) References Cited

U.S. PATENT DOCUMENTS

| | | | |
|---|---|---|---|
| 4,917,099 A | 4/1990 | Stice | |
| 5,022,404 A | 6/1991 | Hafner | |
| 8,273,023 B2 * | 9/2012 | Razavi | .......................... 600/371 |
| 2008/0195169 A1 | 8/2008 | Pinter et al. | |
| 2011/0015503 A1 | 1/2011 | Joffe et al. | |

FOREIGN PATENT DOCUMENTS

| | | |
|---|---|---|
| EP | 0182197 | 5/1986 |
| WO | WO9509028 | 4/1995 |
| WO | WO2006092766 | 9/2006 |

OTHER PUBLICATIONS

Y.Asfaw et al., "Automatic Detection of Detached and Erroneous Electrodes in Electrical Impedance Tomography", School of Information and Technology, University of ottawa, Ottawa, Canada, Un-Dated.

* cited by examiner

Primary Examiner — George Manuel

(57) ABSTRACT

An physiological data acquisition apparatus includes three or more leads, at least one AC current source, a switching mechanism structured to selectively couple the current source to selected lead pairs to inject an AC current across the selected lead pairs which produces an AC voltage across the selected lead pair, and a processing device. The processing device is structured to (i) determine an impedance across the current selected lead pair based on the AC voltage, (ii) determine whether the impedance is less than a predetermined threshold, (iii) if the impedance is less than the predetermined impedance threshold cause the current selected lead pair to be used for generating physiological parameter data, and (iv) if the impedance is not less than the threshold cause the switching mechanism to couple the at least one AC current source to a new selected pair of the leads.

17 Claims, 2 Drawing Sheets

METHOD AND APPARATUS FOR SELECTING DIFFERENTIAL INPUT LEADS

CROSS-REFERENCE TO PRIOR APPLICATIONS

This application is the U.S. National Phase application under 35 U.S.C. §371 of International Application Serial No. PCT/IB2012/052902, filed on Jun. 8, 2012, which claims the benefit of U.S. Provisional Application Ser. No. 61/495,429, filed on Jun. 10, 2011. These applications are hereby incorporated by reference herein.

BACKGROUND OF THE INVENTION

1. Field of the Invention

The present invention relates to physiological data acquisition systems, such as polysomnography systems, and in particular to a method and apparatus for selecting differential input leads for such a system.

2. Description of the Related Art

Polysomnography, also known as a sleep study, is a multiparametric test that is used for the purpose of diagnosing sleep disorders in people. During polysomnography, physiological data is acquired from a patient while he or she sleeps for subsequent analysis by a trained clinician. In a typical polysomnograph, the monitored parameters include such things as electrical encephalographic activity (via an electroencephalogram (EEG)); eye movements (via an electrooculogram (EOG)), muscle activity (via an electromyogram (EMG), heart rhythm (via an electrocardiogram (ECG)), respiratory effort, nasal and/or oral airflow, blood oxygen saturation ($SpO_2$), body position, exhalation $CO_2$, esophageal pH, and breathing sounds (for snoring). These parameters are typically each monitored during sleep by sensors that produce analog signals which are then transmitted to an acquisition device where the data is processed and stored for analysis by a trained clinician.

For a number of the parameters that are monitored during a polysomnograph, the sensors that collect the data are electrical leads that are attached to the patient's body. For example, a polysomnograph often includes collection of EMG data relating to leg movements by attaching leads to the legs of the patient and facial muscle movement and tension by attaching leads to the patient's chin. EEG, EOG, and ECG are also monitored using electrical leads attached to the patient's body.

A recurring problem in polysomnography is the detachment of such leads from the patient during the study as a result of, for example, patient movement during sleep. When a lead becomes detached, a signal is lost from a key sleep parameter or diagnostic indicator, which adversely affects the quality of testing. In addition, detached lead(s), if discovered, require intervention by someone during the study to reattach the lead(s) to the patient. Should the clinician choose to try to reattach the lead(s), they will need to enter the patient's room, turn on the lights, and awaken the patient. This causes a disruption in the patient's sleep and a disruption in the study, since a minimum number of hours of sleep must be recorded. And, again, the clinician will need to repeat the process of traveling back and forth between the patient room and the central control room to assure the impedance is at an acceptable level upon reapplication of the leads.

SUMMARY OF THE INVENTION

Accordingly, it is an object of the present invention to provided a method and apparatus for selecting differential input leads for a physiological data acquisition system which addresses the problem of lead detachment by ensuring that an optimal pair of leads is used for data acquisition.

In one embodiment, an apparatus for acquiring physiological data from a patient is provided that includes three or more leads structured to be placed on a body of the patient, each of the leads being adapted to collect a signal relating to a particular physiological parameter from the patient, at least one AC current source, a switching mechanism structured to selectively couple the at least one AC current source to selected pairs of the leads such that at any one time the at least one AC current source will inject an AC current across only a current selected pair of the leads, wherein in response to the injected AC current, an AC voltage will be generated across the current selected pair of the leads, and a processing device. The processing device is programmed/structured to (i) determine an impedance across the current selected pair of the leads based on the AC voltage, (ii) determine whether the impedance is less than a predetermined impedance threshold, (iii) if the impedance is less than the predetermined impedance threshold cause the current selected pair of the leads to be used for generating data relating to the particular physiological parameter; and (iv) if the impedance is not less than the predetermined impedance threshold cause the switching mechanism to couple the at least one AC current source to a new current selected pair of the leads such that the AC current is injected across the new current selected pair of the leads.

In another embodiment, a method of acquiring physiological data from a patient using three or more leads placed on a body of the patient is provided, wherein each of the leads is adapted to collect a signal relating to a particular physiological parameter from the patient. The method includes injecting an AC current across a first pair of the leads, wherein in response to the injected AC current, a first AC voltage is generated across the first pair of the leads, determining a first impedance across the first pair of the leads based on the first AC voltage, determining that the first impedance is not less than a predetermined impedance threshold, responsive to determining that the first impedance is not less than the predetermined impedance threshold, injecting the AC current across a second pair of the leads, wherein in response to the injected AC current, a second AC voltage will be generated across the second pair of the leads, determining a second impedance across the second pair of the leads based on the second AC voltage, determining that the second impedance is less than the predetermined impedance threshold, and responsive to determining that the second impedance is less than the predetermined impedance threshold, using the second pair of the leads for generating data relating to the particular physiological parameter.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
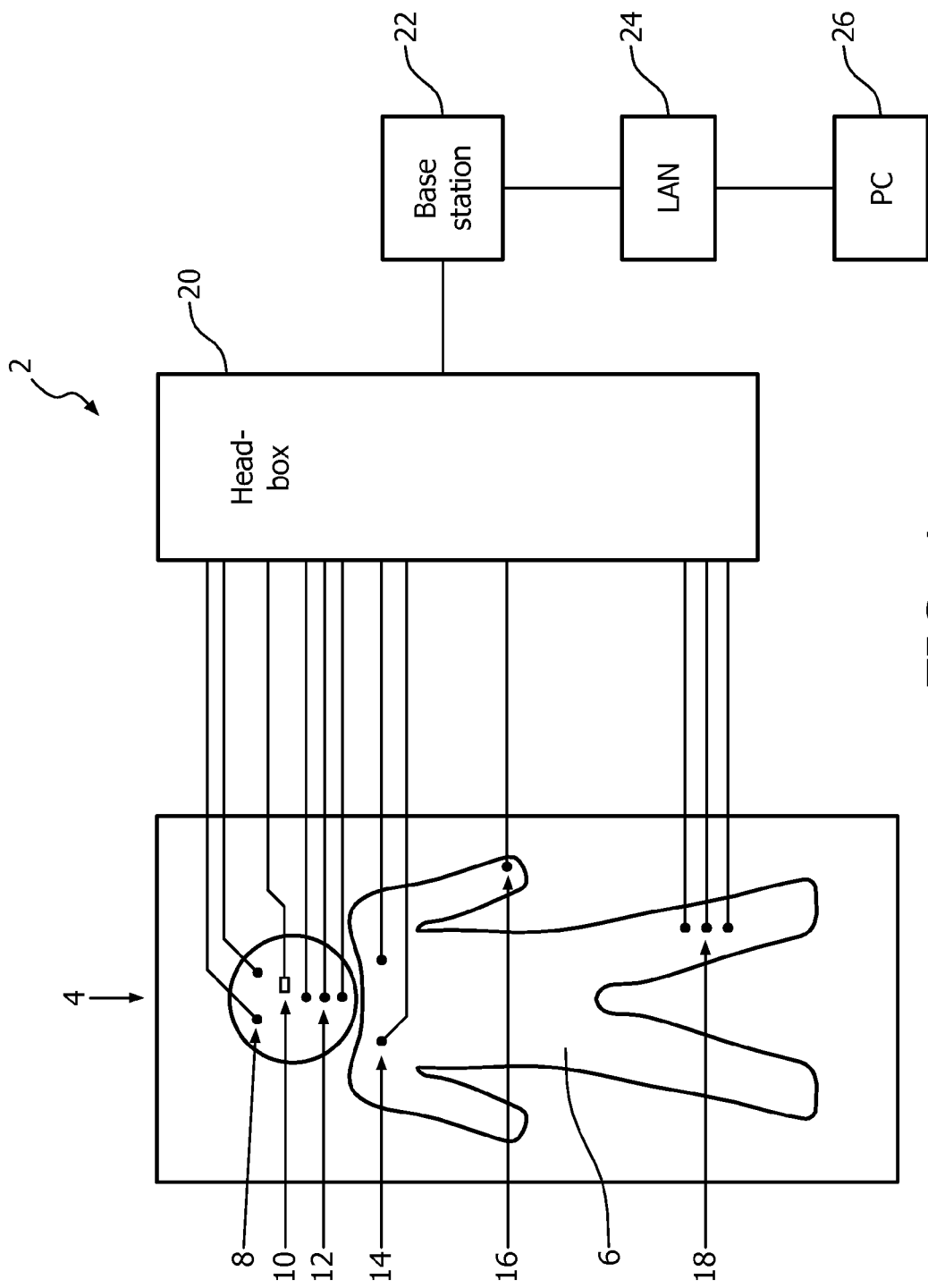
FIG. 1 is a schematic diagram of a polysomnography system according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of a polysomnography system 2 according to an exemplary embodiment of the present invention. As described in greater detail below, polysomnography system 2 employs hardware and software to add redundancy to the sleep diagnostic testing in situations (e.g., EMG, EEG, etc.) wherein a differential pair of leads is needed to make physiological measurements. More particularly, three or more leads are utilized to acquire parameter signals and polysomnography system 2 continuously monitors signal integrity in differential pairs of the leads to sense degradation in a lead(s) (indicative of a wire that has become detached). If degradation is sensed, polysomnography system 2 will attempt to find and switch to an optimal pair of leads for the measurement in question.

Referring to FIG. 1, polysomnography system 2 includes a plurality of exemplary sensors 4 that are operatively coupled to a patient 6 that is undergoing a sleep study. In the exemplary embodiment, sensors 4 include a pair of EOG leads 8 positioned near the eyes of patient 6 for measuring eye movement, a pressure transducer 10 positioned near the nostrils of patient 6 for measuring nasal and/or oral airflow, three EMG leads 12 (12a, 12b, 12c) positioned near the chin of patient 6 for measuring facial muscle actively and tension, a pair of ECG leads 14 positioned on opposite sides of the chest of patient 6 for measuring heart related parameters, an $SpO_2$ sensor 16 positioned on the finger (or, alternatively, the ear) of patient 6 for measuring blood oxygen saturation, and three EMG leads 18 (18a, 18b, 18c) positioned near the leg of patient 6 for measuring leg movements. It should be understood that the particular sensors 4 shown in FIG. 1 are exemplary, and that other sensors in addition to and/or in place of the sensors 4 may also be used in connection with the present invention.

As seen in FIG. 1, polysomnography system 2 further includes a headbox 20 and a base station 22. Each of the sensors 4 is operatively coupled to headbox 20. Headbox 20 is an electronic processing device that receives the analog parameter signal from each of the sensors 4, amplifies and filters each signal and converts each signal to digital form. The digital parameter signals are then output by headbox 20 to base station 22, which is also an electronic processing device. Base station 22 then packetizes the data and further processes and stores the received digital parameter data. In addition, in the exemplary embodiment, base station 22 includes an Ethernet output that enables base station 22 to be connected to a LAN 24. LAN 24 carries the digital parameter data to a central station or tech room where a sleep technician and/or other staff can view and analyze the data on a PC 26 using proprietary host software associated with polysomnography system 2.

Figure 2:
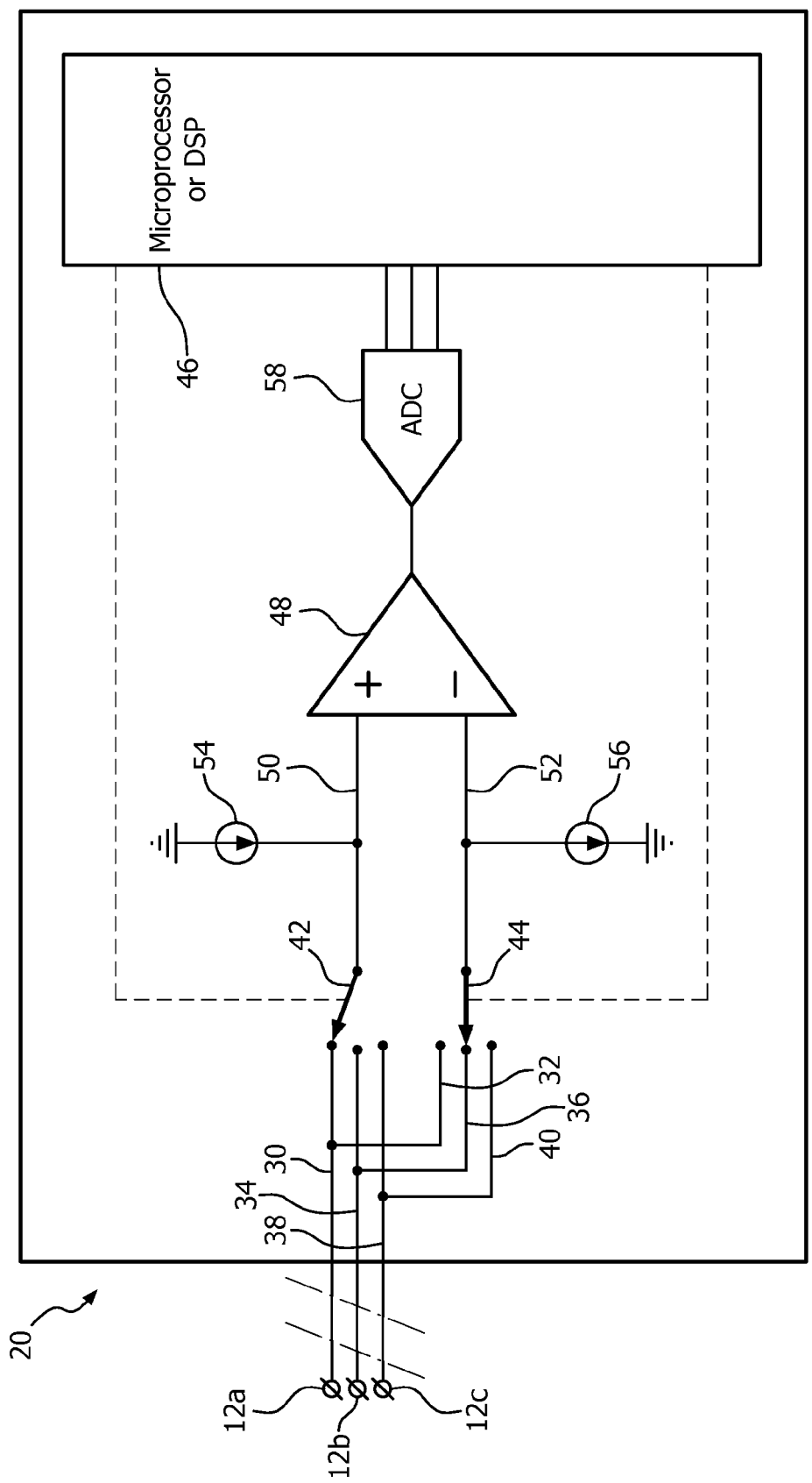
FIG. 2 is a schematic diagram of headbox 20 according to an exemplary embodiment of the present invention.

FIG. 2 is a schematic diagram of headbox 20 according to an exemplary embodiment of the present invention. For purposes of illustrating and describing the present invention, FIG. 2 only shows EMG leads 12a, 12b, 12c being operatively coupled to (i.e., input into) headbox 20. It will be appreciated, however, that as shown in FIG. 1, the other sensors 4 are also operatively coupled to (i.e., input into) headbox 20.

Headbox 20 includes conductors 30 and 32 to which EMG lead 12a is coupled, conductors 34 and 36 to which EMG lead 12b is coupled, and conductors 38 and 40 to which EMG lead 12c is coupled. Headbox 20 also includes programmable analog switch 42 which can be selectively coupled to any one of conductors 30, 34 and 38, and programmable analog switch 44 which can be selectively coupled to any one of conductors 32, 36 and 40. Programmable analog switches 42 and 44 are controlled by a microprocessor or DSP 46 (or another suitable processing device) provided as part of headbox 20 (as shown by the dotted lines in FIG. 2). In addition, headbox 20 includes an instrumentation amplifier 48 or some other suitable differential amplifier device. As seen in FIG. 2, programmable analog switch 42 is also electrically coupled to the non-inverting (+) input of instrumentation amplifier 48 through a conductor 50, and programmable analog switch 44 is also electrically coupled to the inverting (−) input of instrumentation amplifier 48 through a conductor 52. Headbox 20 further includes a first AC current source 54 that is coupled to conductor 50 and a second AC current source 56 that is coupled to conductor 52. First AC current source 54 and second AC current source 56 are structured to output AC current that are 180 degrees out of phase with one another. In the exemplary, non-limiting embodiment, first AC current source 54 and second AC current source 56 is each structured to provide a low level (e.g., 2 nA peak) current set at a particular frequency (e.g., a 100 Hz or a 250 Hz square wave). This current level is well below the safety margins required by IEC 60601-1 and is small enough so as to not adversely impact the physiological data carried by leads 12a, 12b, and 12c. The output of instrumentation amplifier 48 is provided to an analog-to-digital converter (ADC) 58. The output of ADC 58 is provided to microprocessor or DSP 46.

As described below, headbox 20 is adapted to receive input from the three EMG leads 12a, 12b, and 12c and automatically find the first pair of the leads 12a, 12b, and 12c wherein the impedance between the leads is below a preset impedance threshold. An impedance between the pair of leads in question below the preset impedance threshold indicates that neither of the leads of the pair is detached. That pair of leads may then be used to make the EMG measurement that is needed for the polysomnography study.

In operation, an initial, default pair of leads 12a, 12b, 12c is selected by coupling programmable analog switch 42 to a particular one of the leads 12a, 12b, 12c (through the appropriate one of conductors 30, 34 and 38) and coupling programmable analog switch 44 to another particular one of the leads 12a, 12b, 12c (through the appropriate one of conductors 32, 36 and 40). In the exemplary embodiment shown in FIG. 2, that initial, default pair of leads is lead 12a and lead 12b. Current is then injected across the selected pair of leads 12a, 12b by first AC current source 54 and second AC current source 56. As stated above, in the exemplary embodiment, the injected AC current is a low level AC current (e.g., a 2 nA peak current set at a 100 Hz or a 250 Hz square wave). In response to the injected current, an AC voltage will be generated across leads 12a, 12b that is proportional to the impedance between the leads 12a, 12b. That voltage difference is input into and differentially measured by instrumentation amplifier 48. More specifically, as will be appreciated by those of skill in the art, instrumentation amplifier 48 will output an AC voltage that is equal to the difference in the voltage at its two inputs (+ and −) multiplied by a gain factor. Thus, the output of instrumentation amplifier 48 will be an AC voltage that is proportional to the impedance between the leads 12a, 12b because it is equal to the AC voltage across leads 12a, 12b multiplied by the gain factor of instrumentation amplifier 48.

Next, the AC voltage output by instrumentation amplifier 48 is passed to ADC 58 where it is converted to digital form. The digital version of the AC voltage output by instrumentation amplifier 48 is then provided to microprocessor or DSP 46. Inside microprocessor or DSP 46, the digital AC voltage is first narrow band pass filtered (digitally). The narrow band pass filtering extracts the portion/component of the voltage signal that corresponds to and represents the voltage generated in response to the injected AC current and thus that corresponds to and represents the impedance between the selected leads 12a, 12b. The narrow band pass filtering does not pass the portion/component of the voltage signal that corresponds to physiological parameter measures by leads 12a, 12b (EMG in the exemplary embodiment). The narrow band pass filtered signal is then fully rectified (digitally) inside microprocessor or DSP 46. The peak voltage of the rectified signal is measured and converted to an impedance value that represents the impedance between the leads 12a, 12b using a standard linear mathematical translation. The translation can be stated as $Z=mV+b$, where Z is the translated impedance value, V is the measured voltage level, and m and b are the slope and intercept of the linear translation. The values of m and b are a function of the circuit used to create the injected AC current, and are determined in practice by a calibration process which measures the observed voltage level, V, for specific known impedance values Z.

The resulting impedance value is then compared to the preset impedance threshold. In the exemplary embodiment, the preset impedance threshold is 5000 ohms, although other values may also be appropriate depending on the particulars of the application. If the resulting impedance value is less than the preset impedance threshold, then leads 12a, 12b are deemed to be in satisfactory condition and polysomnography system 2 will use leads 12a, 12b as good leads. This means headbox 20 will extract the EMG signal from the leads 12a, 12b, using a digital notch filtering process, and will pass that digital data on to base station 22 for further processing as discussed elsewhere herein. If, however, the resulting impedance value is not less than the preset impedance threshold, then leads 12a, 12b are deemed to not be a good pair. In response, microprocessor or DSP 46 will select a different pair of the leads 12a, 12b, 12c (e.g., 12a and 12c) by controlling programmable analog switches 42, 44 to couple to the selected leads and the verification process just described will be repeated to determine whether that pair of leads is good.

This process will continuously cycle through the three possible lead pair combinations (12a and 12b, 12a and 12c, 12b and 12c) until a satisfactory pair is found or until the study is concluded.

In an alternative exemplary embodiment, when the digital AC voltage signal is received in microprocessor or DSP 46 from ADC 58, a Discrete Fourier Transform (DFT) or a Fast Fourier Transform (FFT) is performed on the signal. The power level of the DFT or FFT output is then measured at the frequency that corresponds to the frequency of the injected AC current (e.g., 100 Hz or 250 Hz). That power level is then converted to an impedance value that represents the impedance between the leads 12a, 12b using a standard linear mathematical translation similar to the translation used for the main exemplary embodiment. The slope, m, and the intercept, b, of the alternative exemplary embodiment translation function would likewise be determined by a calibration process which measures the observed power level, V, for specific known impedance values Z. The resulting impedance value is then compared to the preset impedance threshold and processing and operation proceeds as described in connection with the main exemplary embodiment.

It should be appreciated that the present invention as just described in connection with above exemplary embodiments is not limited to using just three leads. Rather, more than three leads examined in pairs as just described may also be used to add further redundancy to polysomnography system 2.

Furthermore, while the present invention has been described in connection with EMG leads 12 shown in FIG. 1, it should be appreciated that it may also be used with leads that measure other parameters or make measurements at other locations. For example, as noted elsewhere herein, three EMG leads 18 are positioned near the leg of patient 6 for measuring leg movements. Those three leads 18 may be coupled to a circuit configuration within headbox 20 that is identical to that shown in FIG. 2 so that headbox 20 can find a satisfactory pair of the leads 18 by automatically finding the first pair of the leads 18 wherein the impedance between the leads is below a preset impedance threshold as described above. Also, the present invention may be applied to leads other than EMG leads. For example, an additional one or more EOG leads 8 or ECG leads 14 may be provided (resulting in three or more of such leads) so that the present invention may be employed in connection with EOG and/or ECG measurements.

Moreover, the present invention is not limited to in connection with polysomnography, but may also be used with other physiological data acquisition systems and applications. For example, and without limitation, the present invention may be employed in dedicated EEG systems and/or studies or dedicated EMG systems and/or studies.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus for acquiring physiological data from a patient, comprising:
    three or more leads structured to be placed on a body of the patient, each of the leads being adapted to collect a signal relating to a particular physiological parameter from the patient;
    at least one AC current source;
    a switching mechanism structured to selectively couple the at least one AC current source to selected pairs of the leads such that at any one time the at least one AC current source will inject an AC current across only a current selected pair of the leads, wherein in response to the injected AC current, an AC voltage will be generated across the current selected pair of the leads; and
    a processing device structured to (i) determine an impedance across the current selected pair of the leads based on the AC voltage, (ii) determine whether the impedance is less than a predetermined impedance threshold, (iii) if the impedance is less than the predetermined impedance threshold cause the current selected pair of the leads to be used for generating data relating to the particular physiological parameter; and (iv) if the impedance is not less than the predetermined impedance threshold cause the switching mechanism to couple the at least one AC current source to a new current selected pair of the leads such that the AC current is injected across the new current selected pair of the leads.

2. The apparatus according to claim 1, wherein in response to the AC current being injected across the new current selected pair of the leads, a new AC voltage will be generated across the new current selected pair of the leads, wherein the processing device is further structured to (v) determine a new impedance across the new current selected pair of the leads based on the new AC voltage, (vi) determine whether the new impedance is less than the predetermined impedance threshold, (vii) if the new impedance is less than the predetermined impedance threshold cause the new current selected pair of the leads to be used for generating data relating to the particular physiological parameter; and (iv) if the new impedance is not less than the predetermined impedance threshold cause the switching mechanism to selectively couple the at least one AC current source to a second new current selected pair of the leads such that the AC current is injected across the second new current selected pair of the leads.

3. The apparatus according to claim 1, wherein the switching mechanism comprises a first programmable analog switch and a second programmable analog switch each coupled to and under the control of the processing device.

4. The apparatus according to claim 1, further comprising a differential amplifier coupled to the switching mechanism and an analog-to-digital converter coupled to the differential amplifier, wherein the differential amplifier is structured to receive the AC voltage and in response thereto output an amplified AC voltage, wherein the analog-to-digital converter is structured to receive the amplified AC voltage and convert the amplified AC voltage to digital AC voltage data, and wherein the processing device is structured to receive the digital AC voltage data and determine the impedance across the current selected pair of the leads using the digital AC voltage data.

5. The apparatus according to claim 4, wherein the processing device is structured to determine the impedance across the current selected pair of the leads by filtering the digital AC voltage data to produce filtered data, rectifying the filtered data to produce rectified voltage data, determining a peak voltage from the rectified voltage data, and determining the impedance across the current selected pair of the leads based on the peak voltage.

6. The apparatus according to claim 4, wherein the processing device is structured to determine the impedance across the current selected pair of the leads by performing a Discrete Fourier Transform (DFT) or a Fast Fourier Transform (FFT) on the digital AC voltage data to produce a DFT or FFT output, determining a power level of the DFT or FFT output at a frequency that corresponds to a frequency of the injected AC current, and determining the impedance across the current selected pair of the leads based on the power level.

7. The apparatus according to claim 1, wherein the three or more leads are selected from the group consisting of EMG leads, ECG leads and EOG leads.

8. The apparatus according to claim 1, wherein the at least one AC current source comprises a first AC current source structured to output a first AC current and a second AC current source structured to output a second AC current 180 degrees out of phase with the first AC current, the first AC current and the second AC current together forming the AC current that is injected across the current selected pair of the leads.

9. The apparatus according to claim 7, wherein the first and second AC currents are each 2 nA currents comprising a 100 Hz or 250 Hz square wave.

10. A polysomnography system including the apparatus according to claim 1 for acquiring the physiological data from the patient, the physiological data being used to perform a sleep study of the patient.

11. A method of acquiring physiological data from a patient using three or more leads placed on a body of the patient, each of the leads being adapted to collect a signal relating to a particular physiological parameter from the patient, the method comprising:
    injecting an AC current across a first pair of the leads, wherein in response to the injected AC current, a first AC voltage is generated across the first pair of the leads;
    determining a first impedance across the first pair of the leads based on the first AC voltage;
    determining that the first impedance is not less than a predetermined impedance threshold;
    responsive to determining that the first impedance is not less than the predetermined impedance threshold, injecting the AC current across a second pair of the leads, wherein in response to the injected AC current, a second AC voltage is generated across the second pair of the leads;
    determining a second impedance across the second pair of the leads based on the second AC voltage;
    determining that the second impedance is less than the predetermined impedance threshold; and
    responsive to determining that the second impedance is less than the predetermined impedance threshold, using the second pair of the leads for generating data relating to the particular physiological parameter.

12. The method according to claim 11, wherein the determining the first impedance comprises differentially measuring the first AC voltage to produce a first measured AC voltage, filtering and rectifying the first measured AC voltage to produce a first filtered and rectified signal, determining a first peak voltage from the first filtered and rectified signal, and determining the first impedance based on the first peak voltage, and wherein the determining the second impedance comprises differentially measuring the second AC voltage to produce a second measured AC voltage, filtering and rectifying the second measured AC voltage to produce a second filtered and rectified signal, determining a second peak voltage from the second filtered and rectified signal, and determining the second impedance based on the second peak voltage.

13. The method according to claim 11, wherein the determining the first impedance comprises differentially measuring the first AC voltage to produce a first measured AC voltage, performing a Discrete Fourier Transform (DFT) or a Fast Fourier Transform (FFT) on the first measured AC voltage to produce a first DFT or FFT output, determining a first power level of the first DFT or FFT output at a frequency that corresponds to a frequency of the injected AC current, and determining the first impedance based on the first power level, and wherein the determining the second impedance comprises differentially measuring the second AC voltage to produce a second measured AC voltage, performing a Discrete Fourier Transform (DFT) or a Fast Fourier Transform (FFT) on the second measured AC voltage to produce a second DFT or FFT output, determining a second power level of the second DFT or FFT output at the frequency that corresponds to the frequency of the injected AC current, and determining the second impedance based on the first power level.

14. The method according to claim 11, wherein the three or more leads are selected from the group consisting of EMG leads, ECG leads and EOG leads.

15. The method according to claim 11, wherein the AC is generated using a first AC current source structured to output a first AC current and a second AC current source structured to output a second AC current 180 degrees out of phase with the first AC current.

16. The method according to claim 15, wherein the first and second AC currents are each 2 nA currents comprising a 100 Hz or 250 Hz square wave.

17. The method according to claim 11, further comprising using the data relating to the particular physiological parameter is a polysomnography study.

* * * * *